(12) United States Patent
Partika et al.

(10) Patent No.: US 7,648,028 B2
(45) Date of Patent: Jan. 19, 2010

(54) ADAPTER FOR MULTIPLE CAPACITY NEEDLE IMMOBILIZING DEVICE

(75) Inventors: Larry Partika, Bridgewater, NJ (US); Douglas Paddock, Hardyston, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 495 days.

(21) Appl. No.: 11/409,385

(22) Filed: Apr. 21, 2006

(65) Prior Publication Data

US 2008/0221516 A1 Sep. 11, 2008

Related U.S. Application Data

(60) Provisional application No. 60/674,016, filed on Apr. 22, 2005.

(51) Int. Cl.
*B65D 83/10* (2006.01)
(52) U.S. Cl. .................... 206/366; 206/370; 604/110
(58) Field of Classification Search ................ 206/363, 206/364, 365, 366, 370; 211/85.13; 604/110, 604/192; 29/240
See application file for complete search history.

(56) References Cited

U.S. PATENT DOCUMENTS

| | | | |
|---|---|---|---|
| 4,928,917 A | 5/1990 | Wolf | |
| 4,981,476 A | 1/1991 | Aichlmayr et al. | |
| 4,986,811 A | 1/1991 | Thead et al. | |
| 4,986,817 A * | 1/1991 | Code | 604/192 |
| 5,002,536 A | 3/1991 | Thompson et al. | |
| 5,021,049 A | 6/1991 | Howard | |
| 5,047,019 A * | 9/1991 | Sincock | 604/192 |
| 5,099,992 A * | 3/1992 | Heimreid | 206/366 |
| 5,183,469 A | 2/1993 | Capaccio | |
| 5,187,850 A * | 2/1993 | McCammon et al. | 29/235 |
| 5,190,532 A | 3/1993 | Yu | |
| 5,249,679 A * | 10/1993 | Dondlinger | 206/366 |
| 5,417,659 A | 5/1995 | Gaba | |
| 5,469,964 A | 11/1995 | Bailey | |
| 5,483,973 A | 1/1996 | Benson et al. | |
| 5,533,974 A | 7/1996 | Gaba | |
| 5,584,809 A | 12/1996 | Gaba | |
| 6,123,193 A | 9/2000 | Vojtasek et al. | |
| 6,382,417 B2 | 5/2002 | Kanner et al. | |

* cited by examiner

*Primary Examiner*—David T Fidei
(74) *Attorney, Agent, or Firm*—Jeanne P. Lukasavage (57) ABSTRACT

An adapter for a multiple capacity needle immobilizing device having a body portion and entry holes for allowing the distal ends of sharp needles to enter the body includes a base having a top portion and a bottom portion. The bottom portion having apertures positioned to align with the entry holes of the immobilizing device. A non-circular funnel projects upwardly from each of the entry holes to a funnel opening in the top portion of the adapter. The funnel opening is larger when measured perpendicularly to a line extending through the apertures of the adapter than when measured along this line. Structure is provided for connecting the adapter to the needle immobilizing device.

14 Claims, 9 Drawing Sheets

ADAPTER FOR MULTIPLE CAPACITY NEEDLE IMMOBILIZING DEVICE

CROSS-REFERENCE TO RELATED APPLICATIONS

The present invention claims priority of U.S. Provisional Patent Application, Ser. No. 60/674,016, filed on Apr. 22, 2005.

FIELD OF THE INVENTION

The present invention relates to needle trapping or immobilizing devices which accept the sharp ends of used needle cannula and other sharps for the purpose of preventing needle stick injuries. More particularly, the subject invention relates to an adapter for multiple capacity needle immobilization devices.

BACKGROUND

Most hypodermic needles and other procedural needles are provided with needle shields or covers to project the needle from damage during pre-use shipping and handling and to protect health care workers from accidental needle sticks involving clean, unused needles. The needle shield or cover is usually removed immediately prior to its intended use.

After use, the sharp distal tip of the needle is exposed and can be involved in accidental needle sticks which can result in injury to the user and/or the transfer of disease or infection.

Reshielding of the needle with its original shield is discouraged because of the possibility of the user sticking his hand while attempting to reshield. Sticks can result from missing the opening in the shield or having a needle penetrate the side of the shield and stick the user. Even if the needle shield has a broad entry to guide the needle, potential for piercing the entry and the resulting needle stick is present. To avoid these problems, a wide variety of safety devices has been developed. Many of these involve separate hinged or telescoping shields on the medical device or, in some cases, retracting needles which are activated after use. To avoid infection or disease from the used sharps, all devices, even those with additional safety features, should be disposed of as soon as possible after use into an appropriate sharps container.

In many cases, such as in surgical procedures, a variety of needles are used alone or attached to a medical device which does not have additional safety shielding structure. Many surgical procedures are supported by sterile procedure trays containing all of the needles and sharps for the procedure in question. Protecting the sharp distal ends of these needles and sharps has been partially addressed by the prior art which teaches needle receiving structures into which the used needle is inserted. These devices provide structure to shield the distal end of the needle and provide varied amounts of retention force to prevent a needle from inadvertently exiting the device. Such devices are taught in U.S. Pat. No. 5,417,659 to Gaba. The device taught is a single, individual receptacle having internal elements for aggressively holding the contaminated sharps after insertion. U.S. Pat. No. 6,382,417 to Kanner et al. teaches the advantages of having a multiple receptacle needle immobilizing device for use in a procedural tray. The device of Kanner et al. teaches five aligned relatively close, needle receiving portions. This device allows up to five contaminated needle products to be disposed of as a unit in an efficient manner. This device also presents some problems in that long spinal needles are difficult to insert in to the device without holding the shaft of the used and possibly contaminated needles to guide the tip into the receiving aperture of the device.

Although the prior art has provided many solutions for protecting used needles after use, there is still a need for a simple straightforward easy to manufacture needle immobilization device for procedural trays which can easily be used with both short and long needle cannula without requiring the user to touch a contaminated needle to guide into the device.

SUMMARY OF THE INVENTION

An adapter for a multiple capacity needle immobilizing device having a body portion and at least two linearly aligned entry holes for allowing the distal ends of sharp needles to enter the body portion comprises a base including a top portion and a bottom portion. The bottom portion has at least two apertures positioned to align with the at least two entry holes of the needle of the immobilizing device. The apertures are equal or smaller in size than the entry holes in the immobilizing device in order to provide a step-free transition of the needle into the needle immobilizing device. A non-circular funnel projects upwardly from each of the entry holes to a funnel opening in the top portion of the adapter. The funnel is larger when measured perpendicularly from a line extending through the apertures than it is when measured along the line itself. Structure is provided for connecting the adapter to the needle immobilizing device.

The structure for connecting the adapter to the needle immobilizing device includes a downwardly projecting arm on the adapter configured to engage the immobilizing device. Two downwardly projecting arms are preferred. The downwardly projecting arm is configured to engage the immobilizing device in a snap-fit arrangement or in frictional engagement.

A preferred shape of the funnel opening is a substantially rectangular shape preferably having four substantially flat sidewalls. The funnel may also be elliptically shaped and contain a combination of circular and flat sidewalls. It is preferred that the adapter be made of thermoplastic materials with polycarbonate, glass filled nylon and acrylic being preferred.

DETAILED DESCRIPTION

Referring to FIGS. 1-10, a prior art multiple capacity needle immobilizing device 20 includes a body portion 21 having at least two linearly aligned entry holes for allowing the distal ends of sharp needles to enter the body portion. Structure internal to the immobilizing device for trapping or holding the needle is not shown. In this embodiment, the immobilizing device includes five linearly aligned entry holes 26.

Figure 1:
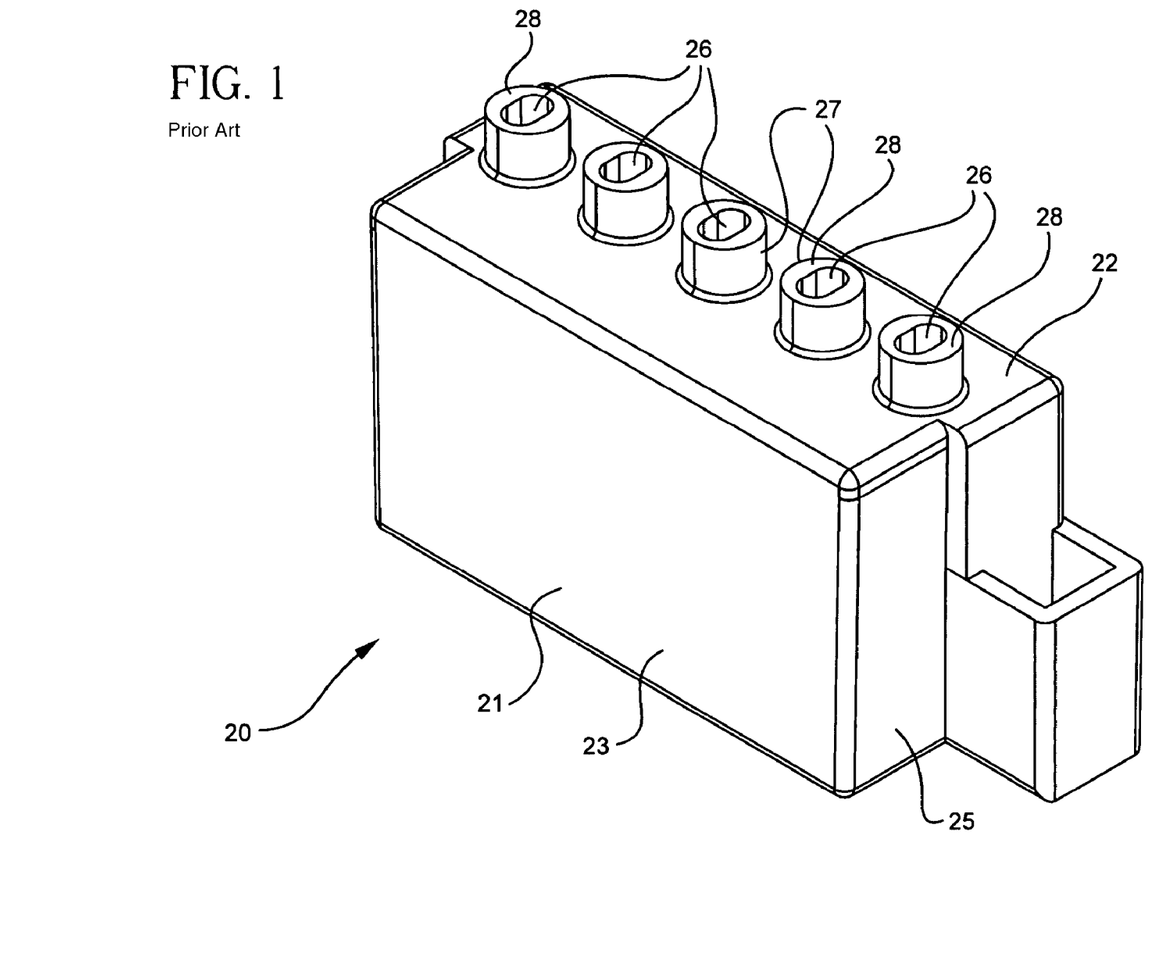
FIG. 1 is a perspective view of a prior art needle immobilization device.
Figure 2:
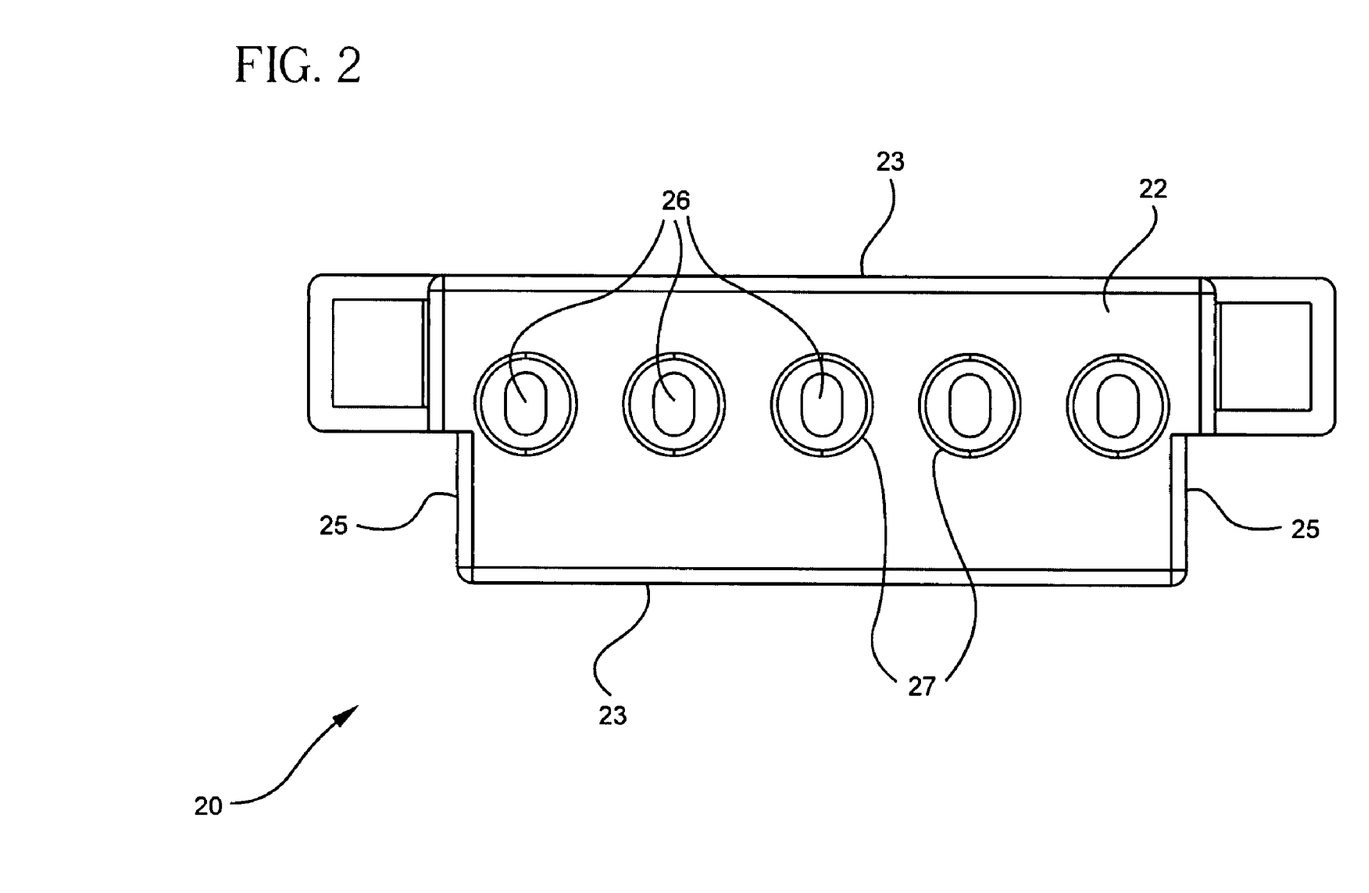
FIG. 2 is a top plan view of the device of FIG. 1.
Figure 3:
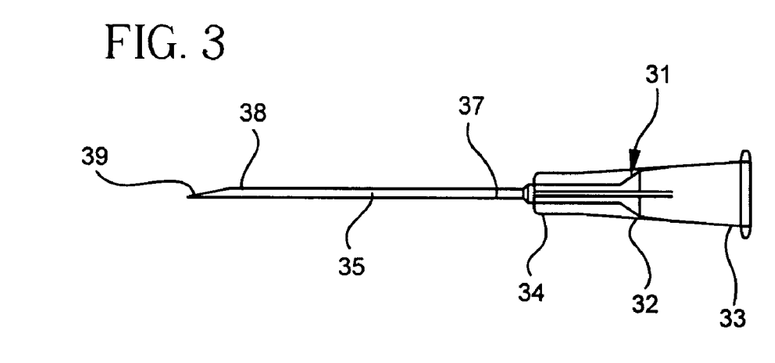
FIG. 3 is a side elevational view of a needle assembly for use with hypodermic syringes and other medical devices.

A commonly used hypodermic needle assembly 31 includes a hub 32, a distal end 34 and a proximal end 33 with a frusto-shaped cavity therein for engaging the tip of a hypodermic syringe or other medical device. A needle 35 includes a proximal end 37, a distal end 38, a lumen therethrough (not shown) and a sharp distal tip 39. Proximal end 37 of the needle is connected to distal end 34 of the hub so that the lumen is in fluid communication with the cavity and the hub.

Figure 4:
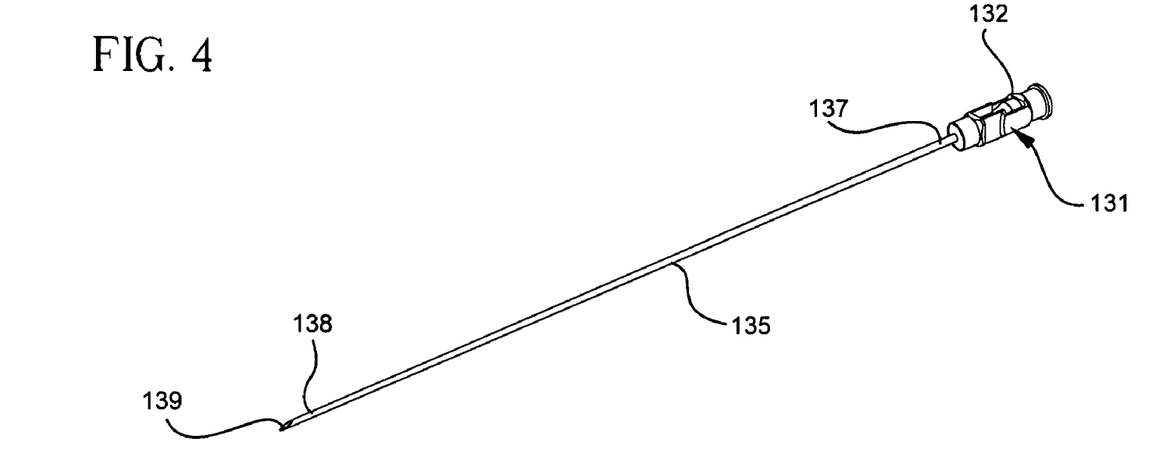
FIG. 4 is a perspective view of a spinal needle.

A commonly used prior art anesthesia needle assembly 131 includes a hub 132 having a cavity therein and a needle 135. The needle includes a proximal end 137, a distal end 138 and a lumen (not shown) therethrough. The proximal end of the needle is attached to the hub so that the lumen is in fluid communication with the cavity and the hub. Although needle lengths vary widely, it should be noted that a needle on a hypodermic needle assembly can be about 16 mm to 38 mm in length (0.63 inch to 1.5 inches). The length of the needle on an anesthesia needle assembly can be between 75 mm-100 mm (3 inches to 4 inches) in length.

An adapter 40 for use with immobilizing device 20 includes a base 41 having a top portion 43 and a bottom portion 44. The bottom portion includes at least two apertures positioned to align with at least two entry holes of the immobilizing device. In this embodiment, there are five apertures 45 positioned to align with the five entry holes 26 of the immobilizing device. The size of apertures 45 is equal or smaller than the entry holes 26 in order to provide a step-free transition of a needle into the immobilizing device. A non-circular funnel 46 projects upwardly from each of entry hole 45 to a funnel opening 47 in top portion 43 of the base. The funnel opening is larger when measured perpendicularly from a line 49 extending through apertures than when measured along the line. Structure is also provided for connecting adapter 40 to needle immobilizing device 20. A wide variety of structures may be provided for connecting the adapter to the needle immobilizing device for example, the needle immobilizing device illustrated includes a raised boss 27 surrounding each of the five entry holes 26. The adapter includes five downwardly projecting sleeves 50 each of which surround boss 27 on the immobilizing device. The connection between the adapter and the immobilizing device can be achieved by a frictional interference fit arrangement between the inside of downwardly projecting sleeves 50 in the adapter and the outside of some or all of bosses 27 on the immobilizing device. This can be achieved by making the inside of the downwardly projecting sleeve slightly smaller than the outside of the bosses. It is not necessary that the connection between the adapter and the immobilizing device be permanent but only secure enough to keep the adapter in place during normal use of the immobilizing device. A permanent or more aggressive connection is desirable but not necessary.

Figure 5:
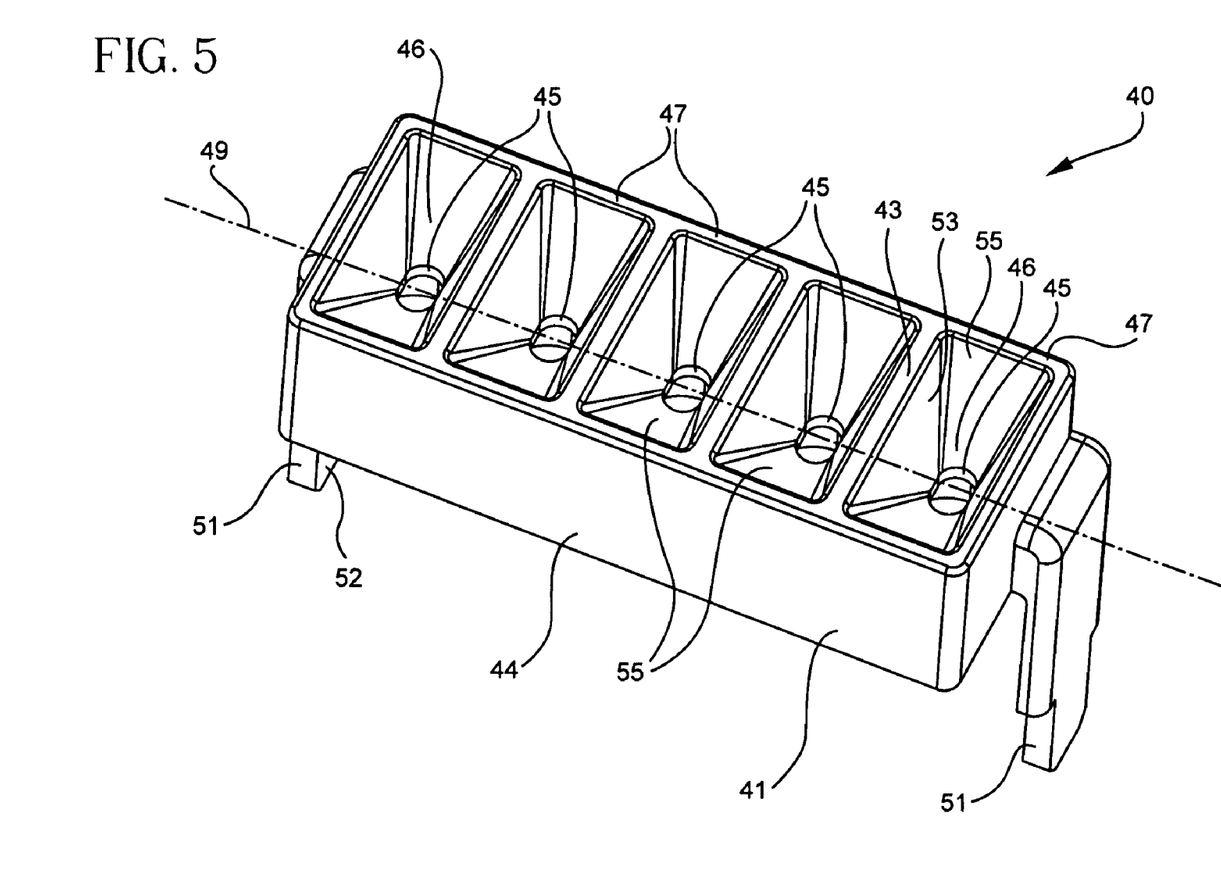
FIG. 5 is a perspective view of the adapter for a multiple capacity needle immobilization devices of the present invention taken from the top.
Figure 6:
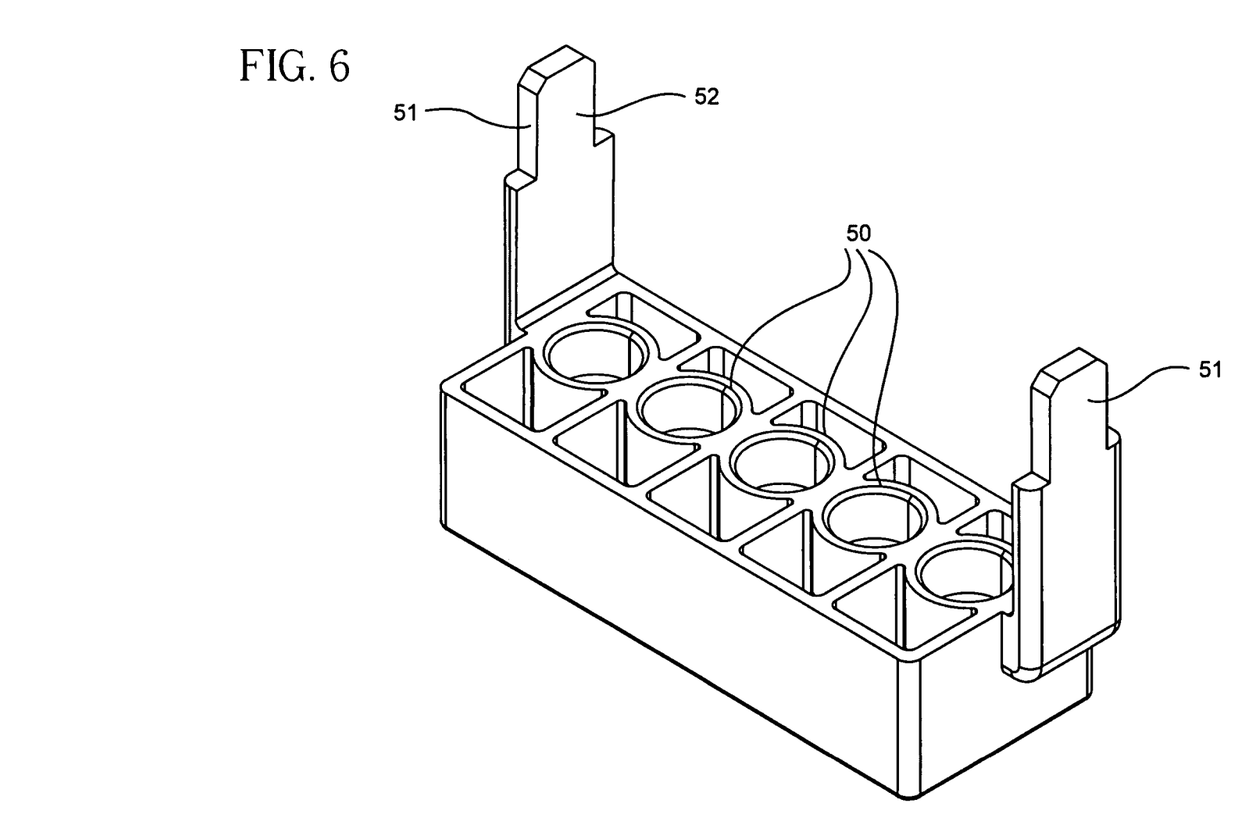
FIG. 6 is a perspective view of the adapter of FIG. 5 taken from the bottom.
Figure 7:
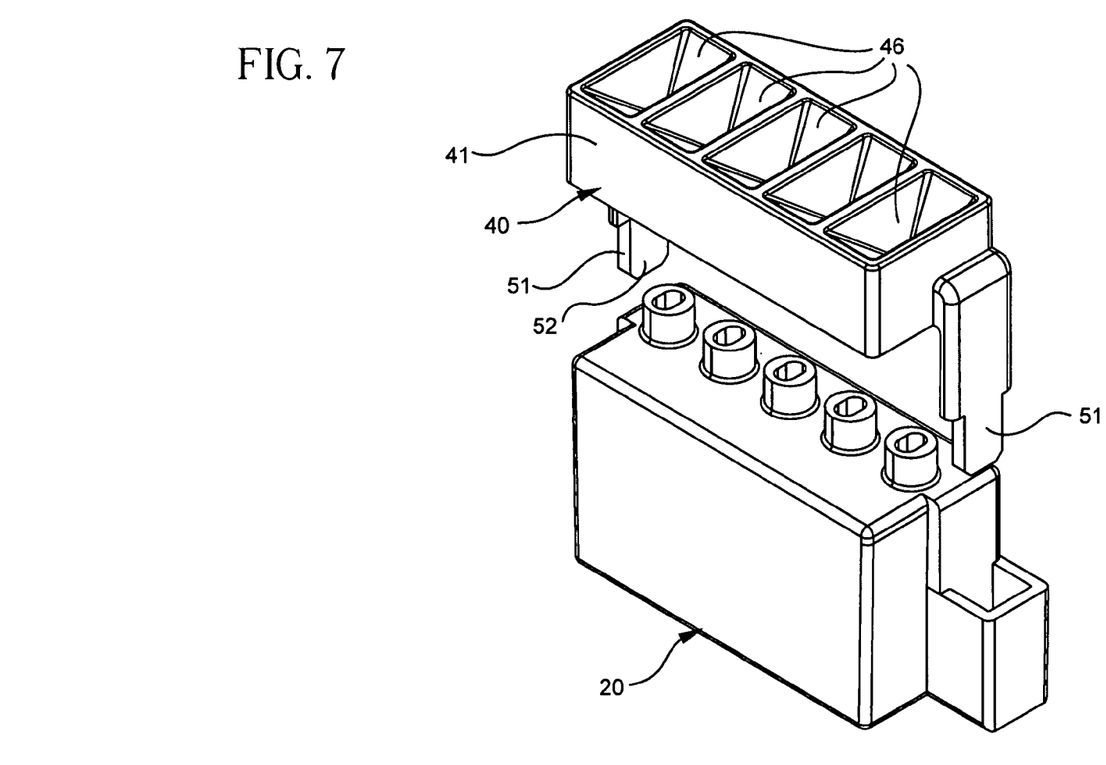
FIG. 7 is a perspective view illustrating the adapter of the present invention being installed on a multiple capacity needle immobilization device.
Figure 8:
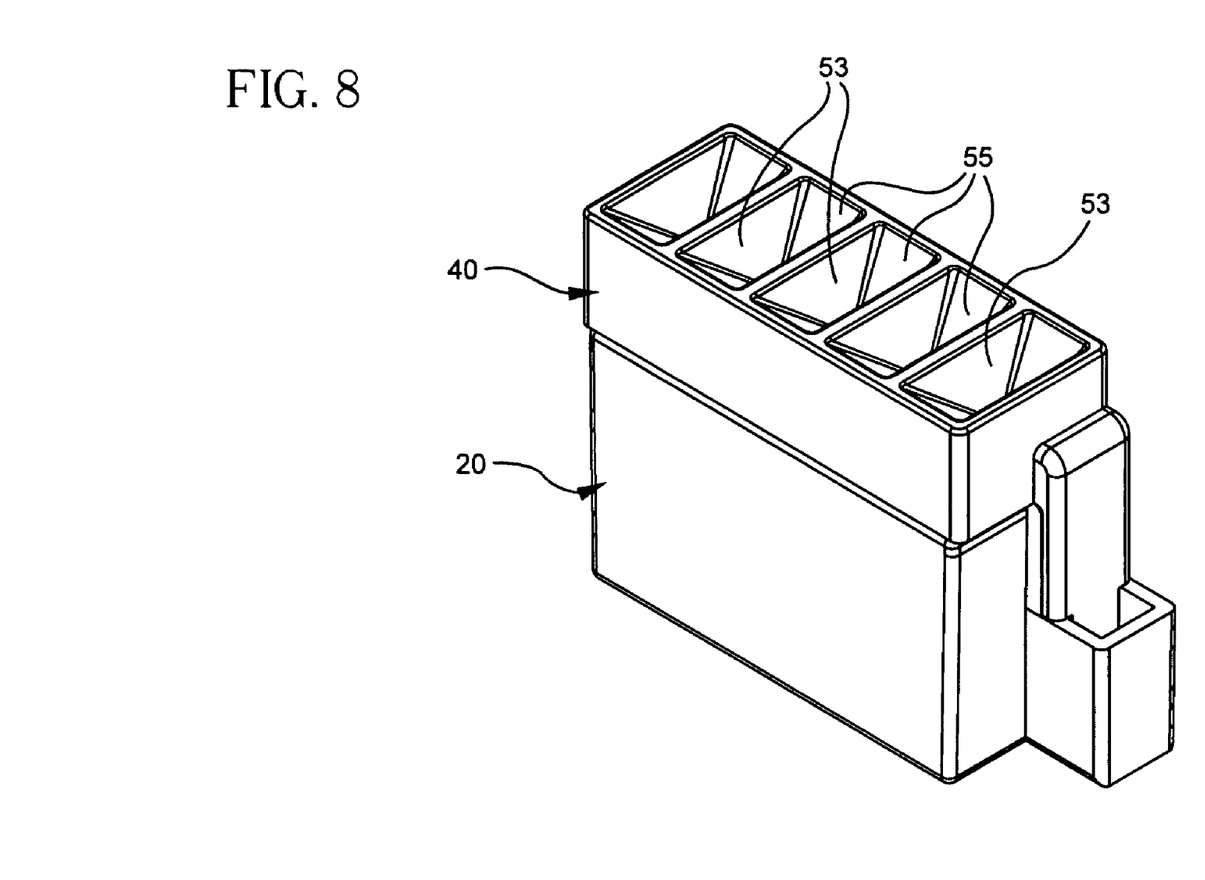
FIG. 8 illustrates the adapter of the present invention fully installed on the multiple capacity immobilization device.

The base of adapter 40 may include downwardly projecting arm configured to engage the immobilizing device. In this embodiment, base 41 of adapter 40 includes two downwardly projecting arms 51 for engaging the immobilizing device. The downwardly projecting arms provide a clear indication of the orientation of the adapter with respect to the immobilizing device. In this embodiment, the distance between interior surface 52 on each of the downwardly projecting arms is slightly less than the length of the immobilizing device providing for a frictional interference fit between the adapter and the immobilizing device. A snap-fit arrangement is preferred if the immobilizing device has a distinguishing feature that will allow such an engagement. If this is the case, a projection can be provided on each of the downwardly projecting arms or on other parts of the adapter, to engage the surface discontinuity on the adapter giving a positive connection along with, if the design permits, an audible indication of engagement as the projections on the downwardly projecting arms of the adapter engage the surface discontinuities of the immobilizing device.

There are many structures and configurations suitable for connecting the adapter to the immobilizing device including the use of metal clips in the adapter, adhesive and the like. These many possibilities are all within the purview of the present invention with those means for connecting taught herein being merely representative of these many possibilities.

Figure 9:
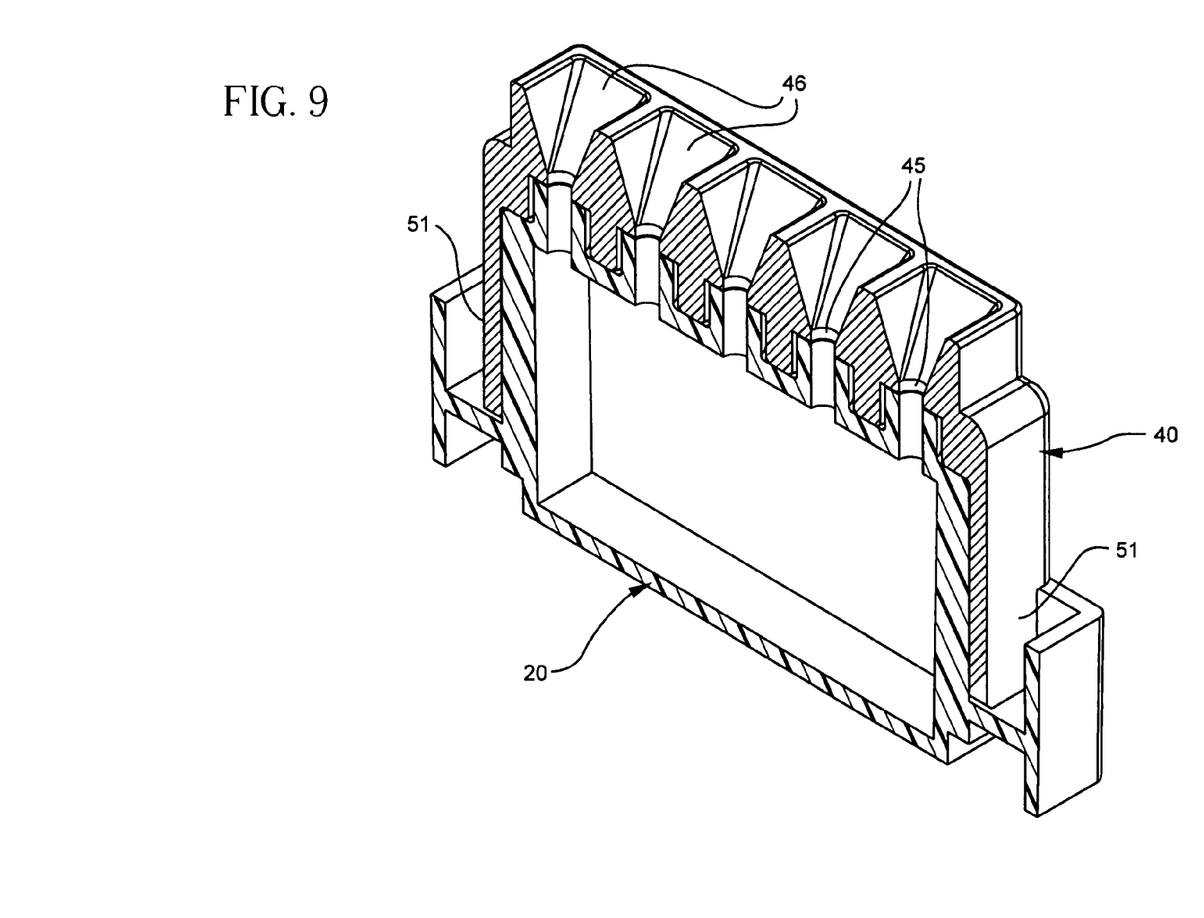
FIG. 9 is a perspective cross-sectional view of the adapter and device of FIG. 8 taken along the major axis of the adapter.
Figure 10:
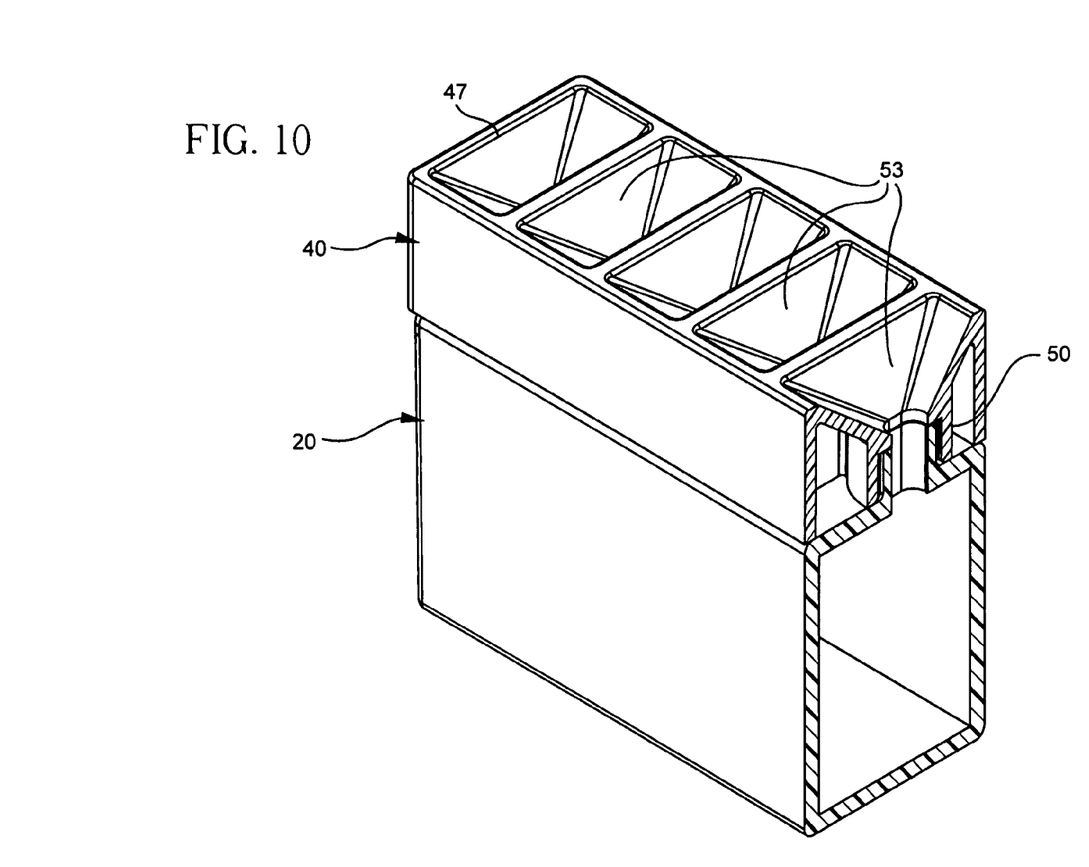
FIG. 10 is a perspective cross-sectional view of the adapter and device of FIG. 8 taken along a minor axis of the adapter.

The adapter of the present invention is ideally suited for use with a needle immobilizing device in a surgical procedure tray containing one or more anesthesia needles. When using the prior art needle immobilizing device 20 with a needle assembly such as needle assembly 31, the user may hold the needle by its hub or the medical device connected to the needle and guide the needle to a vacant entry hole 26 for placement until proper disposal can be achieved. The user must be careful not to stick the sharp point of the needle into top surface 28 on the boss 27. When anesthesia needles are involved, this process becomes more difficult because of the long needle is difficult to guide by holding the hub of the anesthesia needle assembly. Immobilization can be achieved by holding the anesthesia needle by the shaft of the needle in order to guide it into the entry hole. This practice is not recommended or desirable since the needle may contain blood-borne pathogens or other detrimental compounds that can be transferred to the user's hand. The adapter of the present invention is provided to help avoid these problems and allow the use of relatively compact multiple capacity needle immobilizing devices with long needle assemblies such as anesthesia needle assemblies. To facilitate the placement of the tip of the anesthesia needle in the immobilizing device, adapter 40 includes non-circular funnel 46 projecting upwardly from each of the entry holes in the adapter. To maximize the area for needle insertion into the immobilizing device, the funnels are given a non-circular shape. The shape increases the target size for the needle. The opening is maximized along the line of the apertures and even longer direction perpendicular to line 49. This configuration maximizes the target area for needle entry into apertures 45 of the adapter while being consistent with the space limitations of the application. This is especially true in surgical procedure trays where large immobilizing devices would not be practical.

The preferred funnel opening is substantially rectangularly shaped having four substantially flat sidewalls at up to four substantially flat sidewalls indicated as sidewalls 53 along line 49 and sidewalls 55 perpendicular to line 49. Such a configuration maximizes the target to guide the needle into one of the apertures 45 while still maintaining a compact size desirable for some applications, such as surgical procedure trays.

A wide variety of shapes can be used for the funnel opening such as an elliptically shaped funnel opening or combinations of flat and curved sidewalls. The embodiment having four substantially flat sidewalls is preferred. The adapter is desirably made of thermoplastic material. Other materials such as polycarbonate, glass filled nylon and acrylic are preferred since they reduce the chances of a sharp needle tip embedding itself in the funnel sidewall.

What is claimed is:

1. An adapter for a multiple capacity needle immobilizing device having a body portion and at least two linearly aligned entry holes for allowing the distal ends of sharp needles to enter the body portion comprising:
   a base including a top portion and a bottom portion, said bottom portion having at least two apertures positioned to align with the at least two entry holes of the needle immobilizing device, said apertures being equal or smaller than the entry holes in the immobilizing device in order to provide a step-free transition of a needle into the needle immobilizing device, a non-circular funnel projecting upwardly from each of said at least two entry holes to a funnel opening in said top portion, said funnel opening being larger when measured perpendicularly from a line extending through said apertures than when measured along said line; and
   a downwardly projecting arm on said adapter configured to engage said needle immobilizing device.

2. The adapter of claim 1 wherein said base is configured to frictionally engage said immobilizing device.

3. The adapter of claim 1 wherein said downwardly projecting arm is configured to engage said immobilizing device in a snap-fit arrangement.

4. The adapter of claim 1 wherein said downwardly projecting arm is configured to frictionally engage said immobilizing device.

5. The adapter of claim 1 wherein said downwardly projecting arm includes two downwardly projecting arms.

6. The adapter of claim 1 wherein said funnel opening is substantially rectangularly shaped.

7. The adapter of claim 6 wherein said funnel includes four substantially flat sidewalls.

8. The adapter of claim 1 wherein said adapter is made of thermoplastic material.

9. The adapter of claim 1 wherein said adapter is made of material selected from the group consisting of polycarbonate, glass filled nylon and acrylic.

10. The adapter of claim 1 wherein said at least two apertures includes five apertures.

11. An adapter for a needle immobilizing device having a body portion and five linearly aligned entry holes for allowing the distal ends of sharp needles to enter the body portion comprising:
    a plastic base including a top portion and a bottom portion, said bottom portion, said bottom portion having five apertures positioned to align with the five holes of the needle immobilizing device, said apertures being equal or smaller than the entry holes in the immobilizing device in order to provide a step-free transition of a needle into the needle immobilizing device, a non-circular funnel projecting upwardly from each of said five entry holes to a funnel opening in said top portion, said funnel opening being larger when measured perpendicularly from a line extending through said apertures then when measured along said line; and
    means for connecting said adapter to the needle immobilizing device including two arms projecting downwardly from said base of said adapter.

12. The adapter of claim 11 wherein said funnel openings are substantially rectangularly shaped and each funnel including four substantially flat sidewalls converging on side entry holes.

13. The adapter of claim 11 wherein the adapter is made of material selected from the group consisting of polycarbonate, glass filled nylon and acrylic.

14. The adapter of claim 11 wherein said downwardly projecting arms are configured to frictionally engage said immobilizing device.

* * * * *

UNITED STATES PATENT AND TRADEMARK OFFICE
CERTIFICATE OF CORRECTION

PATENT NO. : 7,648,028 B2 Page 1 of 1
APPLICATION NO. : 11/409385
DATED : January 19, 2010
INVENTOR(S) : Partika et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this

Twenty-eighth Day of December, 2010

David J. Kappos
*Director of the United States Patent and Trademark Office*